United States Patent [19]
Heffe et al.

[11] 3,982,001
[45] Sept. 21, 1976

[54] 4-(3.4-METHYLENE DIOXY PHENYL)-PIPERIDINES

[75] Inventors: Wilhelm Heffe, Neuenegg; Fritz Hunziker; Klaus Thoma, both of Berne, all of Switzerland

[73] Assignee: Sandoz, Inc., E. Hanover, N.J.

[22] Filed: Sept. 19, 1974

[21] Appl. No.: 507,449

[30] Foreign Application Priority Data
Sept. 25, 1973  Switzerland.................... 13718/73

[52] U.S. Cl............................ 424/267; 260/240 K; 260/293.58; 260/293.8
[51] Int. Cl.².................................... C07D 405/04
[58] Field of Search................ 260/293.81, 293.82, 260/293.83, 293.84, 293.58, 240 K; 424/267

[56] References Cited
UNITED STATES PATENTS

| | | | |
|---|---|---|---|
| 2,880,211 | 3/1959 | Elpern | 260/294.3 |
| 2,966,491 | 12/1960 | Pfister et al. | 260/294.3 |
| 2,978,454 | 4/1961 | Elpern | 260/294.3 |
| 3,157,650 | 11/1964 | Habicht | 260/247.1 |
| 3,178,477 | 4/1965 | Seeger et al. | 260/570.5 |
| 3,183,235 | 5/1965 | Zenitz | 260/294 |
| 3,189,600 | 6/1965 | Huebner | 260/239 |
| 3,192,229 | 6/1965 | Biel | 260/326.3 |

*Primary Examiner*—G. Thomas Todd
*Attorney, Agent, or Firm*—Gerald D. Sharkin; Robert S. Honor; Thomas O. McGovern

[57] ABSTRACT

This invention provides new compounds of formula I,

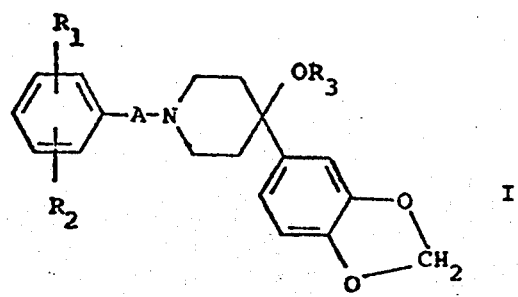

wherein $R_1$ and $R_2$ are the same or different and are in each case hydrogen, halogen, lower alkyl, hydroxy or lower alkoxy $R_3$ is hydrogen or lower acyl and A stands for groups of formula

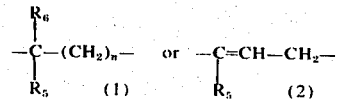

wherein $R_5$ and $R_6$ are independently, hydrogen or methyl and n is 0, 1 or 2, useful as analgesic agents.

39 Claims, No Drawings

4-(3.4-METHYLENE DIOXY PHENYL)-PIPERIDINES

IMPROVEMENTS IN OR RELATING TO ORGANIC COMPOUNDS

The invention relates to new compounds of formula I,

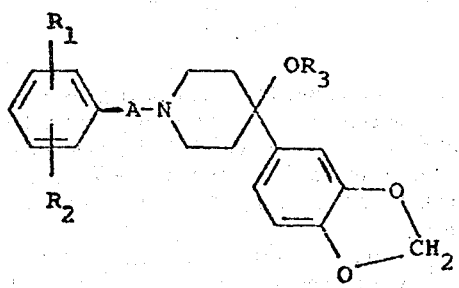

wherein $R_1$ and $R_2$ are the same or different and are in each case hydrogen, halogen, lower alkyl, hydroxy or lower alkoxy $R_3$ is hydrogen or lower acyl and A stands for groups of formula

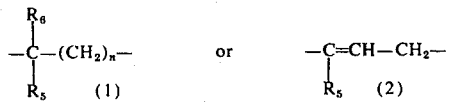

wherein $R_5$ and $R_6$ are independently, hydrogen or methyl and $n$ is 0,1 or 2.

Where in formula I $R_1$ and $R_2$ are alkyl or alkoxy, this is preferably an alkyl group with 1 – 4 carbon atoms, in particular methyl, and alkoxy is preferably in alkoxy group with 1 – 4 carbon atoms, in particular methoxy. Where $R_1$ and $R_2$ are halogen, the halogen is fluorine, chlorine, bromine or iodine, preferably chlorine. The halogen atoms are preferably in the ortho position of the phenyl ring. Where $R_3$ stands for acyl this is preferably an acyl group with 2 – 4 carbon atoms, in particular in acetyl group.

Any carbon-containing radical not specifically defined herein preferably has up to 5 carbon atoms.

According to the invention compounds of formula I can be obtained by a. condensing compounds of formula II,

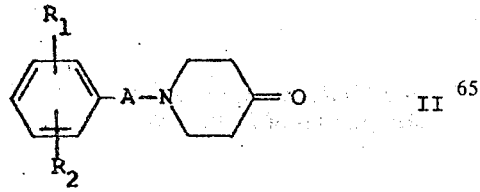

wherein $R_1$, $R_2$ and A are as defined above, with compounds of formula XII,

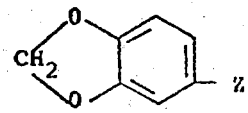

wherein Z is Li or a magnesium halide radical of formula —MgX, wherein X is chlorine, bromine or iodine, to produce a compound of formula Ia,

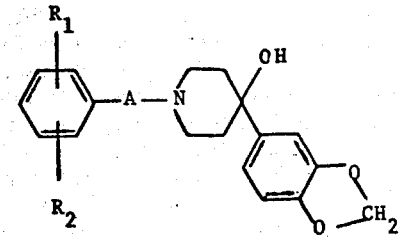

wherein $R_1$, $R_2$ and A are as defined above, b. reacting a compound of formula VI,

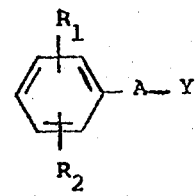

wherein $R_3$ is as defined above, with a compound of formula VII,

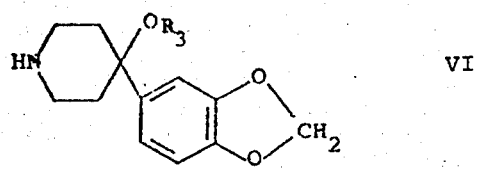

wherein $R_1$, $R_2$ and A are as defined above and Y is a reactive ester of an alcohol, to produce a compound of formula I, or c. acylating a compound of formula Ia to produce a compound of formula Ib,

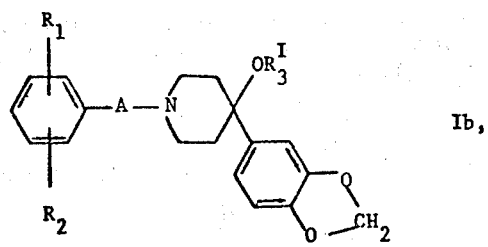

wherein $R_1$, $R_2$ and A are as defined above, and $R_3'$ is acyl.

The process described under a) may be carried out as follows:

The compounds of formula II may be reacted with the compounds of formula XII in an organic solvent which is suitable for Grignard reactions, e.g. ether, such as diethyl ether or tetrahydrofuran, and possibly in an aromatic hydrocarbon, such as benzene. The reaction is conveniently effected at a temperature of between −20° and +80°C, preferably between +20° and +55°C. Hydrolysis of the organometallic complex formed may be carried out in a known way, e.g. by using an aqueous ammonium chloride solution.

The process described under b) may be carried out as follows:

Compounds of formula VI may be reacted with compounds of formula VII, wherein Y is preferably chlorine, iodine or the acid radical of an organic sulphonic acid, e.g. an alkyl sulphonyloxy or an aryl sulphonyloxy radical, but is in particular bromine. The reaction may be effected in an inert organic solvent, e.g. an aromatic hydrocarbon, such as benzene, toluene or xylene, a di (lower alkyl) amide of a lower aliphatic monocarboxylic acid, such as dimethyl formamide, or in a chlorinated aliphatic hydrocarbon, such as chloroform or carbon tetrachloride. An acid-binding agent, e.g. an alkali metal carbonate, such as potassium carbonate or sodium carbonate, or a tertiary amine, such as triethylamine or pyridine, is preferably present when the reaction takes place. However, in place of the acid-binding agents mentioned, an excess of a compound of formula VI may be used, 100% excess of this compound being suitable. To accelerate the reaction, the reaction mixture can be heated and/or mixed thoroughly. The reaction is preferably carried out at a temperature of between 30° and 100°C.

Preferably $R_3$ is hydrogen in process b).

Process variant c) may be carried out in a known way for such acylation reactions, e.g. with the aid of an acylating agent, e.g. the anhydride or acid chloride of an appropriate aliphatic acid. Pyridine may conveniently be present. An elevated temperature, e.g. 100°C, is preferably used.

The compounds of formula II used in the process described in a) as starting compounds can be obtained by reacting compounds of formula III,

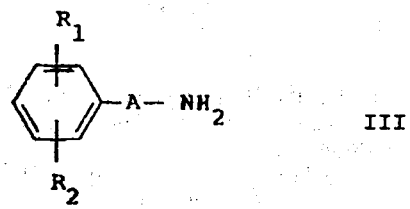

III wherein $R_1$, $R_2$ and A are as defined above, with an acrylic acid ester, subjecting the reaction product of formula IV,

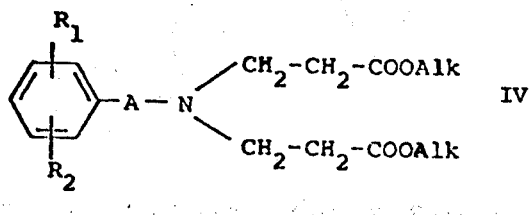

IV wherein $R_1$, $R_2$ and A are defined above and Alk is an alkyl group with 1 – 4 carbon atoms, to a Dieckmann cyclization, saponifying the keto ester formed and decarboxylizing the keto acid obtained in a known way.

The compounds of formula XII used in process a) can be obtained by brominating 1,2-methylene dioxy benzene in a known way, e.g. by reacting with bromosuccinimide, or by chlorinating or iodizing in a known way, and reacting the compounds obtained of formula XIII,

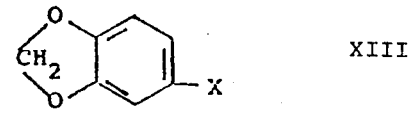

XIII wherein X is as defined above, with magnesium chips in an inert solvent, such as tetrahydrofuran, at a temperature of between 50° and 60°C. The compounds of formula XII, wherein Z is lithium, are produced from compounds of formula XIII by reaction with lithium in a known way.

The compound of formula VI used as starting compound in the process described in b) can be obtained by hydrogenizing a compound of formula V,

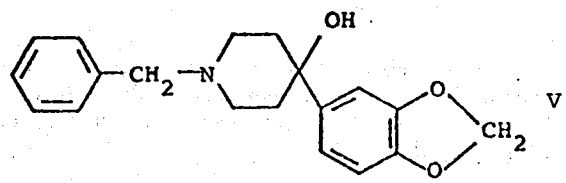

V in the presence of a palladium/carbon catalyst in a known way. The compound of formula V is produced by reacting 1-benzyl-piperidone with compounds of formula XII, e.g. using process variant a)

The compounds of formula VII (wherein A is —CH$_2$—CH$_2$, i.e. group (1), wherein $R_5$ and $R_6$ are hydrogen and n is 1) used in the same process as starting compounds can be obtained in a known way by converting compounds of formula VIII,

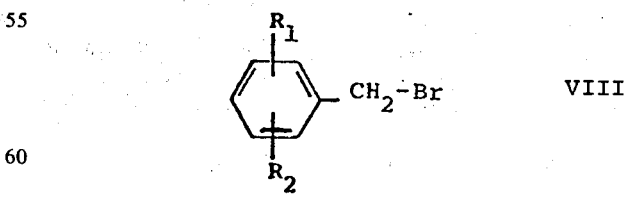

VIII wherein $R_1$ and $R_2$ are as defined above, into the equivalent nitriles of formula IX,

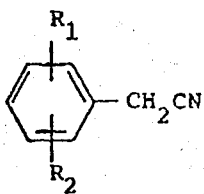

wherein $R_1$ and $R_2$ are as defined above and saponifying these to give compounds of formula X,

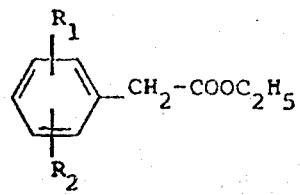

wherein $R_1$ and $R_2$ are as defined above, from which, by reduction with lithium aluminium hydride, compounds are obtained of formula XI,

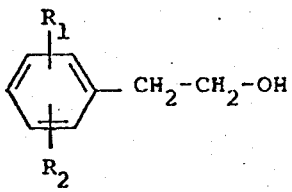

wherein $R_1$ and $R_2$ are as defined above, and these are converted in a known way, e.g. with phosphorous tribromide, where Y stands for bromine, into the corresponding reactive esters of formula VII.

Compounds of formula VII, wherein A is not the —$CH_2$—$CH_2$— group and Y is not bromine, are obtained from the corresponding starting compounds in a known way. The other compounds described as starting compounds in the above processes are either known or can be produced from known starting compounds in a known way.

Free base forms of the compounds of formula I can be converted into acid addition salt forms in conventional manner and vice versa. The organic acids maleic acid, fumaric acid and oxalic acid and the inorganic acids hydrochloric acid and hydrobromic acid are suitable for salt formation.

In the following Examples all temperatures are in degrees Centigrade.

EXAMPLE 1

1-Phenethyl-4-hydroxy-4-(3.4-methylene dioxy phenyl)-piperidine [Process variant b)]

a. 3.4 Methylene dioxy-bromo-benzene

A suspension of 12.2 g. methylene dioxy benzene and 17.8 g. N-bromosuccinimide in 120 ml. chloroform is heated to boiling over the course of 3 hours.

After 20 minutes a clear red brown solution is obtained which becomes a yellow solution after 1½ hours. When boiling is complete, the clear solution obtained is washed with water, dried over sodium sulphate and freed from solvent. The residue is distilled in a vacuum and 3.4-methylene dioxy bromo-benzene with a boiling point of 105°–108°/11 mm. is obtained.

b. 3.4-methylene dioxy-phenyl-magnesium bromide 1.35 g. magnesium chips and 20 ml. tetrahydrofuran are added in a nitrogen atmosphere to a flask provided with a stirrer, a drip funnel, a thermometer and a reflux condenser and a potassium hydroxide drying tube. The whole is then heated to 50° – 60°C and a few drops of bromine and a few drops of a solution of 11 g. 3.4-methylene dioxybromo-benzene in 50 ml. tetrahydrofuran are added. When the reaction has started, the remainder of the methylene dioxy bromo-benzene solution in tetrahydrofuran is added drop by drop for approximately 10 minutes and the resultant mixture is then left to react for 1 hour at 50° – 60°C. The Grignard solution obtained is used immediately for the reaction described below:

c. 1-Benzyl-4-hydroxy-4-(3.4-methylene dioxy phenyl)-piperidine

The Grignard solution obtained in b) is cooled to 30°C and mixed drop by drop over the course of 45 minutes with a solution of 9.5 g. 1-benzyl-4-piperidone in 30 ml. tetrahydrofuran, during which time the temperature of the mixture rises to 32° – 37°C. After mixing is complete, the whole is cooled and then left to react for 1 hour at 20°C and 2 hours at 37° – 40°C. The flask is subsequently rinsed out with nitrogen and the reaction mixture is heavily concentrated in a vacuum. The yellow residue is dissolved in 150 ml. dry ether and the solution is mixed at 10° – 15°C with 100 ml. conc. aqueous ammonium chloride solution while being cooled with ice. The layers formed are separated and the ether solution is washed with an aqueous ammonium chloride solution and twice with water. The ether solution is then dried over sodium sulphate and evaporated to dryness in the rotary evaporator. The residue is recrystallized from isopropanol. The 1-benzyl-4-hydroxy-4-(3.4-methylene dioxy phenyl)-piperidine obtained melts at 147° – 149°C.

d. 4-Hydroxy-4-(3.4-methylene dioxy phenyl)-piperidine 39.4 g. 1-benzyl-4-hydroxy-4-(3.4-methylene dioxy phenyl)-piperidine are dissolved in 400 ml. methanol and the solution is mixed with 30 ml. 4-N hydrochloric acid. To this mixture is then added 3 g. of a palladium/carbon catalyst which has been suspended in 60 ml. alcohol. The mixture is hydrogenized at 35° – 40°C under normal pressure. After 3300 ml. hydrogen has been absorbed, hydrogenation is stopped and the cataylst is removed from the mixture by filtering. The mother liquor is heavily concentrated and the 4-hydroxy-4-(3.4-methylene dioxy phenyl)-piperidine hydrochloride with a melting point of 198° – 200°C crystallizes out.

Base:

35.7 g. of the hydrochloric salt are dissolved in 10 ml. water and the solution is mixed with 69 ml. of a 2N aqueous sodium hydroxide solution. The mixture becomes turbid and the base subsequently crystallizes out. This is filtered by suction and washed with water. The 4-hydroxy-4-(3.4-methylene dioxy phenyl)-piperidine obtained melts at 135° – 138°C.

The mother liquor is saturated with soda and shaken out with ethyl acetate. The ethyl acetate solution is evaporated and the residue is recrystallised from acetone. Additional 4-hydroxy-4-(3.4-methylene dioxy phenyl)-piperidine with a melting point of 136° – 138°C is obtained.

e. 1-Phenethyl-4-hydroxy-4-(3.4-methylene dioxy phenyl)-piperidine 2.2 g. 4-Hydroxy-4-(3.4-methylene dioxy phenyl)-piperidine are dissolved hot in 35 ml. acetone, the solution is mixed with 0.95 g β phenethyl bromide and the reaction mixture is refluxed.

Crystallization starts after 1 hour and is complete after approximately 3 hours. The crystals are filtered off, the filtrate is concentrated a little and heated to boiling over a further 5 hours.

After this it is evaporated to dryness and the residue is extracted three times with 50 ml. ether each time. The ether solutions are combined, concentrated and mixed with petroleum ether, during which time 1-phenethyl-4-hydroxy-4-(3.4-methylene dioxy phenyl)-piperidine with a melting point of 120° – 122°C precipitates.

EXAMPLE 2

1-Phenethyl-4-hydroxy-4-(3.4-methylene dioxy phenyl)-piperidine [Process variant a)]

The Grignard solution obtained in b) of Example 1 is cooled to 35°C and mixed for 45 minutes with a solution of 10.15 g. phenethyl piperidone in 35 ml. tetrahydrofurane, during which time the temperature should not exceed 40°C. When mixing is complete a precipitate forms and the whole is then left to react for a further 2 hours at a temperature of between 38° and 40°C. The reaction vessel is rinsed out with nitrogen and the reaction mixture is heavily concentrated in a vacuum. The residue is mixed with 150 ml. ether and to this mixture is then added drop by drop at 10° – 15°C over the course of 15 minutes 100 ml. of an aqueous concentrated ammonium chloride solution. The layers formed are separated, the ether layer is washed twice with water, dried over sodium sulphate and evaporated to dryness in the rotary evaporator. The residue obtained is 1-phenethyl-4-hydroxy-4-(3.4-methylene dioxy phenyl)-piperidine which, after recrystallization from isopropanol, melts at 123° – 125°C.

EXAMPLE 3

1-Phenethyl-4-propionyloxy-4-(3.4-methylene dioxy phenyl)-piperidine [Process variant c)]

3 g. 1-Phenethyl-4-hydroxy-4-(3.4-methylene dioxy phenyl)-piperidine are dissolved in 4.5 ml. pyridine and the solution obtained is mixed with 4.5 ml. propionic acid anhydride. The resultant mixture is heated for 3 hours on a stream bath, the reaction mixture is then freed from pyridine in a vacuum and the dark oil which remains is extracted twice with 30 ml. water each time. After this the oil is taken up in ether and the ether solution is washed with a 2N aqueous soda solution. The ether solution is then dried over potassium carbonate and evaporated. The residue obtained is mixed with some propanol and water and the mixture is adjusted to neutral with 3 ml. of a 2N hydrochloric acid. Acetone is added and after this the whole is evaporated twice to dryness. The acetone solution is finally mixed with ether during which time 1-phenethyl-4-propionyloxy-4-(3.4-methylene dioxy phenyl)-piperidine hydrochloride precipitates in the form of colourless crystals with a melting point of 180° – 181°C.

EXAMPLE 4

1-Cinnamyl-4-hydroxy-4-(3.4-methylene dioxy phenyl)-piperidine [Process variant b)]

4.4 g. 4-hydroxy-4-(3.4-methylene dioxy phenyl)-piperidine are dissolved hot in 75 ml. acetone, the solution obtained is mixed with 2.5 g. cinnamyl bromide and the reaction mixture is heated at reflux to boiling over the course of 4 hours. After boiling for 1 hour, part of the hydrobromide of the piperidinol used as the starting compound forms a precipitate and this is filtered off on completion of the reaction. The filtrate is then evaporated to dryness and extracted 3 times with 70 ml. ether each time. The ether solutions are combined, concentrated and mixed with petroleum ether during which time 1-cinnamyl-4-hydroxy-4-(3.4-methylene dioxy phenyl)-piperidine with a melting point of 114° – 115°C precipitates.

EXAMPLE 5

1-(2-Chloro-phenethyl)-4-hydroxy-4-(3.4-methylene dioxy phenyl)-piperidine [Process variant a)]

1.31 g. Magnesium chips under 30 ml. absolute tetrahydrofuran are mixed with traces of iodine and methyl iodide and heated to start corrosion. To this mixture is added drop by drop in a nitrogen atmosphere a solution of 10.07 g. 4-bromo-pyrocatechine-methylene ether in 60 ml. absolute tetrahydrofuran. The reaction is started by heating and the temperature of the mixture is adjusted to 50° – 55°C. On completion of the reaction, heating is continued for a further 45 minutes to 55°C. After this the mixture is cooled to 30°C and a solution of 10.7 g. 1-(o-chloro phenethyl)-4-piperidone in 30 ml. absolute tetrahydrofuran is added drop by drop at this temperature with stirring, during which time the temperature rises to 45°C as a result of the exothermic reaction. The mixture is then heated for a further hour to 55°C and a white precipitate forms in the initially clear yellow solution. The tetrahydrofuran is subsequently distilled off in a vacuum and the viscous yellowish residue is divided between a 20% aqueous ammonium chloride solution and ether. The ether phase is washed once with a 20% aqueous ammonium chloride solution and twice with water, dried over sodium sulphate and evaporated to dryness. The residue is clarified in an acetone solution with charcoal and recrystallized from ether/petroleum ether. The 1-(2-chloro-phenethyl)-4-hydroxy-4-3.4-methylene dioxy phenyl)-piperidine obtained melts in the form of colourless crystals at 105° – 106°C.

EXAMPLE 6

4-Hydroxy-4-(3.4-methylene dioxy phenyl)-1-(3-phenyl propyl)-piperidine [Process variant b)]

4.4 g. 4-Hydroxy-4-(3.4-methylene dioxy phenyl)-piperidine are dissolved hot in 70 ml. acetone. 2.2 g. Phenyl propyl bromide are added to the solution obtained and the resultant mixture is heated at reflux to boiling over the course of 3 hours. After this the precipitate which has formed (hydrochloride of the starting amine) is filtered off. The filtrate is cooled and 4-hydroxy-4-(3.4-methylene dioxy phenyl)-1-(3-phenyl propyl)-piperidine with a melting point of 142° – 143°C crystallizes out. Additional 4-hydroxy-4-(3.4-methylene dioxy phenyl)-1-(3-phenyl propyl)-piperidine is obtained by evaporating the filtrate and extracting the residue with ether. After recrystallization from 50 ml. acetone, the melting point of the compound rises to 143° – 144°C.

The following compounds are obtained by using the process described in Example 1 and the corresponding starting compounds:

| Example | $R_1$ | $R_2$ | A | $R_3$ | Melting point |
|---|---|---|---|---|---|
| 7 | 2-Cl | H | $-CH_2-$ | H | 193–195°C (hydrochloride) |
| 8 | 2-Cl | 4-Cl | $-CH_2-CH_2-$ | H | 209–210°C (hydrochloride) |
| 9 | 2-Cl | 6-Cl | $-CH_2-CH_2-$ | H | 204–205°C (hydrochloride) |
| 10 | 2-Cl | H | $-CH_2-CH_2-CH_2-$ | H | 122–123°C (hydrochloride) |
| 11 | H | H | $-\underset{\underset{CH_3}{\vert}}{CH}-CH_2-$ | H | 101–103°C (base) |
| 12 | 3-Cl | H | $-CH_2-CH_2-$ | H | 118–120°C (base) |
| 13 | 4-Cl | H | $-CH_2-CH_2-$ | H | 136–138°C (base) |
| 14 | 2-$CH_3$ | H | $-CH_2-CH_2-$ | H | 127–128°C (base) |
| 15 | 3-$CH_3$ | H | $-CH_2-CH_2-$ | H | 110–112°C (base) |
| 16 | 4-$CH_3$ | H | $-CH_2-CH_2-$ | H | 129–132°C (base) |
| 17 | 2-$CH_3O$ | H | $-CH_2-CH_2-$ | H | 107–109°C (base) |
| 18 | 3-$CH_3O$ | H | $-CH_2-CH_2-$ | H | 121–122°C (base) |
| 19 | 4-$CH_3O$ | H | $-CH_2-CH_2-$ | H | 114–117°C (base) |
| 20 | 4-Cl | H | $-\underset{\underset{CH_3}{\vert}}{\overset{\overset{CH_3}{\vert}}{C}}-CH_2-$ | H | |
| 21 | 3-$CH_3O$ | 4-$CH_3O$ | $-CH_2-CH_2-$ | H | 104–105°C (base) |
| 22 | H | H | $-\underset{\underset{CH_3}{\vert}}{\overset{\overset{CH_3}{\vert}}{C}}-CH_2-$ | H | |
| 23 | 4-F | H | $-CH_2-CH_2-$ | H | 124–125°C (base) |
| 24 | 4-n-$C_3H_7$ | H | $-CH_2-CH_2-$ | H | 121–123°C (base) |
| 25 | 3-OH | 4-$OCH_3$ | $-CH_2-CH_2-$ | H | |
| 25a | 2-F | H | $-CH_2-CH_2-$ | H | 110–111°C (base) |
| 25b | 3-F | H | $-CH_2-CH_2-$ | H | 111–112°C (base) |

The following compounds are obtained analogous to Example 3 and by using appropriate quantities of suitable starting products:

| Example | $R_1$ | $R_2$ | A | $R_3$ | Melting point | |
|---|---|---|---|---|---|---|
| 26 | H | H | $-(CH_2)_2-$ | $-COCH_3$ | 197° C | (hydrochloride) |
| 27 | 2-Cl | H | $-(CH_2)_2-$ | $-COCH_3$ | 201° C | (hydrochloride) |
| 28 | 2-Cl | H | $-(CH_2)_2-$ | $-COC_2H_5$ | 156–158° C | hydrochloride |

The compounds ($R_3$ = H) described in Examples 1, 2 and 4 – 25 can be produced using either the process in Example 2 (process a) or that in Example 4 (process b).

EXAMPLE 29

4-Acetoxy-4-(3.4-methylene dioxy phenyl)-1-(3-phenyl-propyl)-piperidine [process variant b)]

6.9 g. of 4-Acetoxy-4-(3.4-methylene dioxy phenyl)-piperidine hydrochloride in 50 ml water is treated with 11.5 ml 2N sodium hydroxide to give the corresponding free base. The free base is extracted with chloroform, dried with potassium carbonate and obtained as an oil on evaporation under a vacuum. The oil is dissolved in acetone, 2.5 g phenyl propyl bromide is added and the mixture is refluxed for 24 hours. The mixture is worked up as in Example 1e, extracting with ethyl acetate instead of ether and recrystallizing the title compound from isopropanol M.P. 177° – 179°C.

Preparation of starting materials

4-Acetoxy-4-(3.4-methylene dioxy phenyl)-piperidine hydrochloride (M.P. 167° – 168°C) is obtained in analogous manner to that described in Example 1d from 4-Acetoxy-1-benzyl-4-(3.4-methylene dioxy phenyl)-piperidine hydrochloride with no free hydrochloric acid and at a temperature of 40° – 50°C.

4-Acetoxy-1-benzyl-4-(3.4-methylene dioxy phenyl)-piperidine hydrochloride (M.P. 185°C) is obtained from 1-benzyl-4-hydroxy-4-(3.4-methylene dioxy phenyl)-piperidine in a manner analogous to that described in Example 3.

In a manner analogous to that described in Example 1 (process variant b) there is obtained from the appropriate starting materials a compound of formula Ia wherein:

| | $R_1$ | $R_2$ | A |
|---|---|---|---|
| i) | 2-OH | 6-OH | $-\underset{\underset{CH_3}{\vert}}{C}=CH-CH_2-$ |

The compounds of formula I are useful as analgesic agents, as indicated in standard tests, for example, by an inhibition of the phenyl benzoquinone syndrome in mice on p.o. administration of from 3 to 50 mg/kg animal body weight of the compounds, and in the tail flick test in mice on p.o. administration of from 3 to 50 mg/kg animal body weight of the compounds.

For this use the dosage will, of course, vary depending on the compound employed, mode of administration and treatment desired. However, in general, satisfactory results are obtained when administered at a daily dosage of from about 0.4 mg to about 60 mg/kg animal body weight, conveniently given in divided doses 2 to 4 times a day or in sustained release form. For the larger mammals, the total daily dosage is in the range from about 30 to about 350 mg, and dosage forms suitable for oral administration comprise from about 7.5 mg to about 175 mg of the compounds admixed with a solid or liquid pharmaceutical carrier or diluent.

The Example 5 compound shows particularly good activity.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

A preferred tablet composition consists of 30 mg. 1-(2-chloro-phenethyl)-4-hydroxy-4-(3.4-methylene dioxy phenyl)-piperidine, 70 mg. lactose, 5 mg. corn starch, 5 mg. talc and 0.1 mg magnesium stearate.

The compounds of formula I in the present invention which are preferred in respect of their pharmacodynamic effect are particularly those in which $R_1$ and $R_2$ are either chlorine or hydrogen in each case and A is a straight-chain, saturated or unsaturated radical with 2 or 3 carbon atoms, i.e. groups (1) and (2) wherein $R_5$ and $R_6$ is in each case hydrogen and $n$ is 1 or 2.

In a group of compounds $R_1$ and $R_2$ are independently chosen from hydrogen, halogen, alkyl or alkoxy. In another sub group $R_1$ and $R_2$ are independently chosen from hydrogen and chlorine. Preferably at least one of $R_1$ and $R_2$ is in the ortho position. Preferably $R_5$ and $R_6$ are hydrogen.

Preferred compounds are those with $R_3$ hydrogen.

We claim:

1. A compound of the formula,

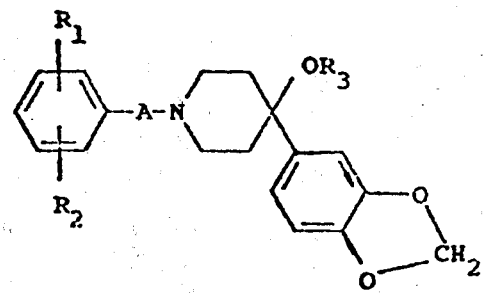

wherein $R_1$ and $R_2$ are the same or different and are in each case hydrogen, halogen, lower alkyl, hydroxy or lower alkoxy $R_3$ is hydrogen and A stands for groups of formula

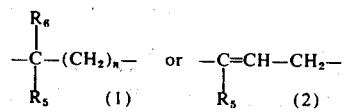

wherein $R_5$ and $R_6$ are independently, hydrogen or methyl and $n$ is 0,1 or 2, or a pharmaceutically acceptable acid addition salt thereof.

2. A compound of claim 1 wherein $R_1$ and $R_2$ are independently chosen from hydrogen, halogen, alkyl or alkoxy.

3. A compound of claim 2 wherein $R_1$ and $R_2$ are independently chosen from hydrogen or chlorine.

4. A compound of claim 1 wherein at least one of $R_1$ and $R_2$ is in the ortho position.

5. A compound of claim 1 wherein $R_5$ and $R_6$ are hydrogen.

6. A compound of claim 1 wherein $n$ is 1 or 2.

7. A compound of claim 1 which is 1-phenethyl-4-hydroxy-4-(3.4-methylene dioxy phenyl)-piperidine.

8. A compound of claim 1 which is 1-cinnamyl-4-hydroxy-4-(3.4-methylene dioxy phenyl)-piperidine.

9. A compound of claim 1 which is 1-(2-Chloro-phenethyl)-4-hydroxy-4-(3.4-methylene dioxy phenyl)-piperidine.

10. A compound of claim 1 which is 4-hydroxy-4-(3.4-methylene dioxy phenyl)-1-(3-phenyl propyl)-piperidine.

11. A compound of claim 1 wherein $R_1$, $R_2$, A and $R_3$ are respectively 2—Cl, H, —CH$_2$—, H.

12. A compound of claim 1 wherein $R_1$, $R_2$, A and $R_3$ are respectively 2—Cl, 4—Cl, —CH$_2$—CH$_2$—, H.

13. A compound of claim 1 wherein $R_1$, $R_2$, A and $R_3$ are respectively 2—Cl, 6—Cl, —CH$_2$—CH$_2$—, H.

14. A compound of claim 1 wherein $R_1$, $R_2$, A and $R_3$ are respectively 2—Cl, H, —CH$_2$—CH$_2$—CH$_2$—, H.

15. A compound of claim 1 wherein $R_1$, $R_2$, A and $R_3$ are respectively H, H,

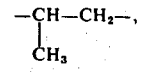

H.

16. A compound of claim 1 wherein $R_1$, $R_2$, A and $R_3$ are respectively 3—Cl, H, —CH$_2$—CH$_2$—, H.

17. A compound of claim 1 wherein $R_1$, $R_2$, A and $R_3$ are respectively 4—Cl, H, —CH$_2$—CH$_2$—, H.

18. A compound of claim 1 wherein $R_1$, $R_2$, A and $R_3$ are respectively 2—CH$_3$, H, —CH$_2$—CH$_2$—, H.

19. A compound of claim 1 wherein $R_1$, $R_2$, A and $R_3$ are respectively 3—CH$_3$, H, —CH$_2$—CH$_2$—, H.

20. A compound of claim 1 wherein $R_1$, $R_2$, A and $R_3$ are respectively 4—$CH_3$, H, —$CH_2$—$CH_2$—, H.

21. A compound of claim 1 wherein $R_1$, $R_2$, A and $R_3$ are respectively 2—$CH_3O$, H, —$CH_2$—$CH_2$—, H.

22. A compound of claim 1 wherein $R_1$, $R_2$, A and $R_3$ are respectively 3—$CH_3O$, H, —$CH_2$—$CH_2$—, H.

23. A compound of claim 1 wherein $R_1$, $R_2$, A and $R_3$ are respectively 4—$CH_3O$, H, —$CH_2$—$CH_2$—, H.

24. A compound of claim 1 wherein $R_1$, $R_2$, A and $R_3$ are respectively 4—Cl, H,

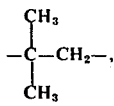

H.

25. A compound of claim 1 wherein $R_1$, $R_2$, A and $R_3$ are respectively 3—$CH_3O$, 4—$CH_3O$, —$CH_2$—$CH_2$—, H.

26. A compound of claim 1 wherein $R_1$, $R_2$, A and $R_3$ are respectively H, H,

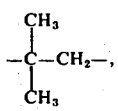

H.

27. A compound of claim 1 wherein $R_1$, $R_2$, A and $R_3$ are respectively 4—F, H, —$CH_2$—$CH_2$—, H.

28. A compound of claim 1 wherein $R_1$, $R_2$, A and $R_3$ are respectively 4—n—$C_3H_7$, H, —$CH_2$—$CH_2$—, H.

29. A compound of claim 1 wherein $R_1$, $R_2$, A and $R_3$ are respectively 3—OH, 4—$OCH_3$, —$CH_2$—$CH_2$—, H.

30. A compound of claim 1 wherein $R_1$, $R_2$, A and $R_3$ are respectively 2—F, H, —$CH_2$—$CH_2$—, H.

31. A compound of claim 1 wherein $R_1$, $R_2$, A and $R_3$ are respectively 3—F, H, $CH_2$—$CH_2$—, H.

32. A compound of claim 1 which is 1-benzyl-4-hydroxy-4-(3,4-methylene dioxy phenyl)-piperidine.

33. A pharmaceutical composition useful in the treatment of pain comprising 30 to 350 milligrams of a compound of claim 1 in association with a pharmaceutical carrier or diluent.

34. A pharmaceutical composition according to claim 33 comprising 7.5 to 175 milligrams of the compound per unit dosage.

35. A pharmaceutical composition according to claim 33 in which the compound is 1-(2-chlorophenethyl)-4-hydroxy-4-(3,4-methylenedioxyphenyl)-piperidine.

36. A method of treating pains in animals, which comprises administering to an animal in need of such treatment a therapeutically effective amount of a compound of claim 1.

37. A method according to claim 36 in which 30 to 350 milligrams of the compound are administered daily.

38. A method according to claim 36 in which 7.5 to 150 milligrams of the compound are administered per unit dose.

39. A method according to claim 36 in which the compound is 1-(2-chlorophenethyl)-4-hydroxy-4-(3,4-methylenedioxyphenyl)-piperidine.

* * * * *